(12) United States Patent
Flatt et al.

(10) Patent No.: US 7,402,663 B2
(45) Date of Patent: Jul. 22, 2008

(54) MODIFIED PEPTIDE

(75) Inventors: Peter Raymond Flatt, Portrush (GB); Finbarr Paul Mary O'Harte, Portstewart (GB)

(73) Assignee: University of Ulster, Coleraine, County Londonderry (GB)

( * ) Notice: Subject to any disclaimer, the term of this patent is extended or adjusted under 35 U.S.C. 154(b) by 499 days.

(21) Appl. No.: 10/469,655

(22) PCT Filed: Feb. 28, 2002

(86) PCT No.: PCT/GB02/00827

§ 371 (c)(1),
(2), (4) Date: Feb. 5, 2004

(87) PCT Pub. No.: WO02/070546

PCT Pub. Date: Sep. 12, 2002

(65) Prior Publication Data

US 2004/0116657 A1   Jun. 17, 2004

(30) Foreign Application Priority Data

Mar. 1, 2001   (GB) ................................. 0105069.9

(51) Int. Cl.
*A61K 38/00*  (2006.01)
*A61K 38/04*  (2006.01)
*C07K 1/00*  (2006.01)
*C07K 5/00*  (2006.01)
*C07K 7/00*  (2006.01)
*C07K 16/00*  (2006.01)
*C07K 17/00*  (2006.01)

(52) U.S. Cl. ........................... 530/402; 530/328; 514/2; 424/1.69

(58) Field of Classification Search ................... 530/402
See application file for complete search history.

(56) References Cited

U.S. PATENT DOCUMENTS 5,128,448 A   7/1992   Danho et al.
5,631,230 A   5/1997   Fang et al.
6,924,264 B1 *   8/2005   Prickett et al. ................. 514/2

FOREIGN PATENT DOCUMENTS

DE   18 00 129 A   5/1969
DE   19 35 402 A   1/1970
DE   276 482 A   2/1990

OTHER PUBLICATIONS

M. Rodriguez et al., "Synthesis and biological activity of pseudopeptide analogues of the C-terminal heptapeptide of cholecystokinin. On the importance of the peptide bonds.", *Journal of Medicinal Chemistry* 30:8 (Aug. 1987) pp. 1366-1373, American Chemical Society. Washington.
M. Rodriguez et al., "Synthesis and biological activity of some partially modified retro-inverso analogues of cholecystokinin", Journal of Medicinal Chemistry 32:10, pp. 2331-2339 (Oct. 1989) American Chemical Society, Washington.
R. Gonzalez-Muniz et al., "Solid phase synthesis of a fully active analogue of cholecystokinin using the acid-stable OC-Phe (p-CH2) SO3H as a substitute for Boc-Tyr (SO3H) in CCK8", *International Journal of Peptide and Protein Research*, vol. 37, pp. 331-340 (1991) Munksgaard, Copenhagen, DK.
O'Harte, Finbarr P. M. et al., "Glycated cholecystokinin-8 has an enhanced satiating activity and is protected against enzymic degradation", *Diabetes* 47(10), 1619-1624 (1998).
M-C Galas et al., "Structure-Activity Relationship Studies On Cholecystokinin Analogues With Partial Agonist Activity", *American Journal of Physiology* 254:2 Part 1 (1988) pp. G176-G182.
Kuwahara A et al., "Effects Of Cholecystokinin Octapeptide On Gastric Motility Of Anesthetized Dogs", *American Journal of Physiology*, 251:5 Part 1 (1986) pp. G678-G681.

* cited by examiner

*Primary Examiner*—Cecilia Tsang
*Assistant Examiner*—Maury Audet
(74) *Attorney, Agent, or Firm*—Licata & Tyrrell PC

(57) ABSTRACT

The invention provides a peptide based on biologically active CCK-8 having improved characteristics for the treatment of obesity and/or type 2 diabetes wherein the primary structure of CCK-8 is: $Asp^1Tyr^2(SO_3H)$-$Met^3Gly^4Trp^5Met^6Asp^7$ $Phe^8$amide (SEQ ID NO:1) and wherein the peptide has at least one amino add substitution and/or modification and is not $Asp^1$-glucitol CCK-8. The invention also provides the use of the peptide in the preparation of a medicament to inhibit food intake, induce satiety, stimulate insulin secretion, moderate blood glucose excursions, enhance glucose disposal and/or exhibit enhanced stability in plasma compared to native CCK-8 and/or for treatment of obesity and/or type 2 diabetes.

4 Claims, 12 Drawing Sheets

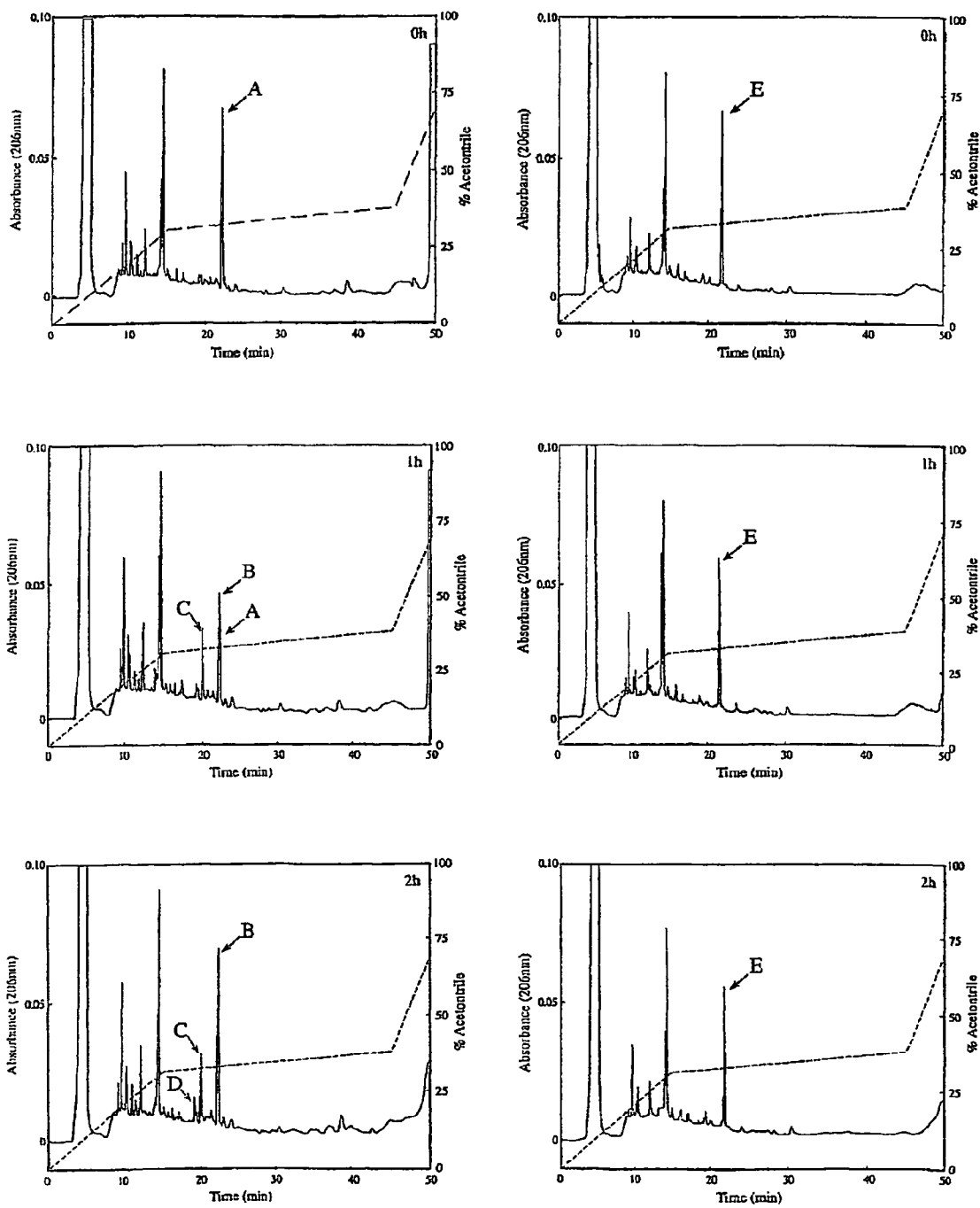
Fig. 1. HPLC profiles of CCK-8 and Asp1-glucitol CCK-8 following incubation with serum for 0, 1 and 2 h on a Vydac C-18 column

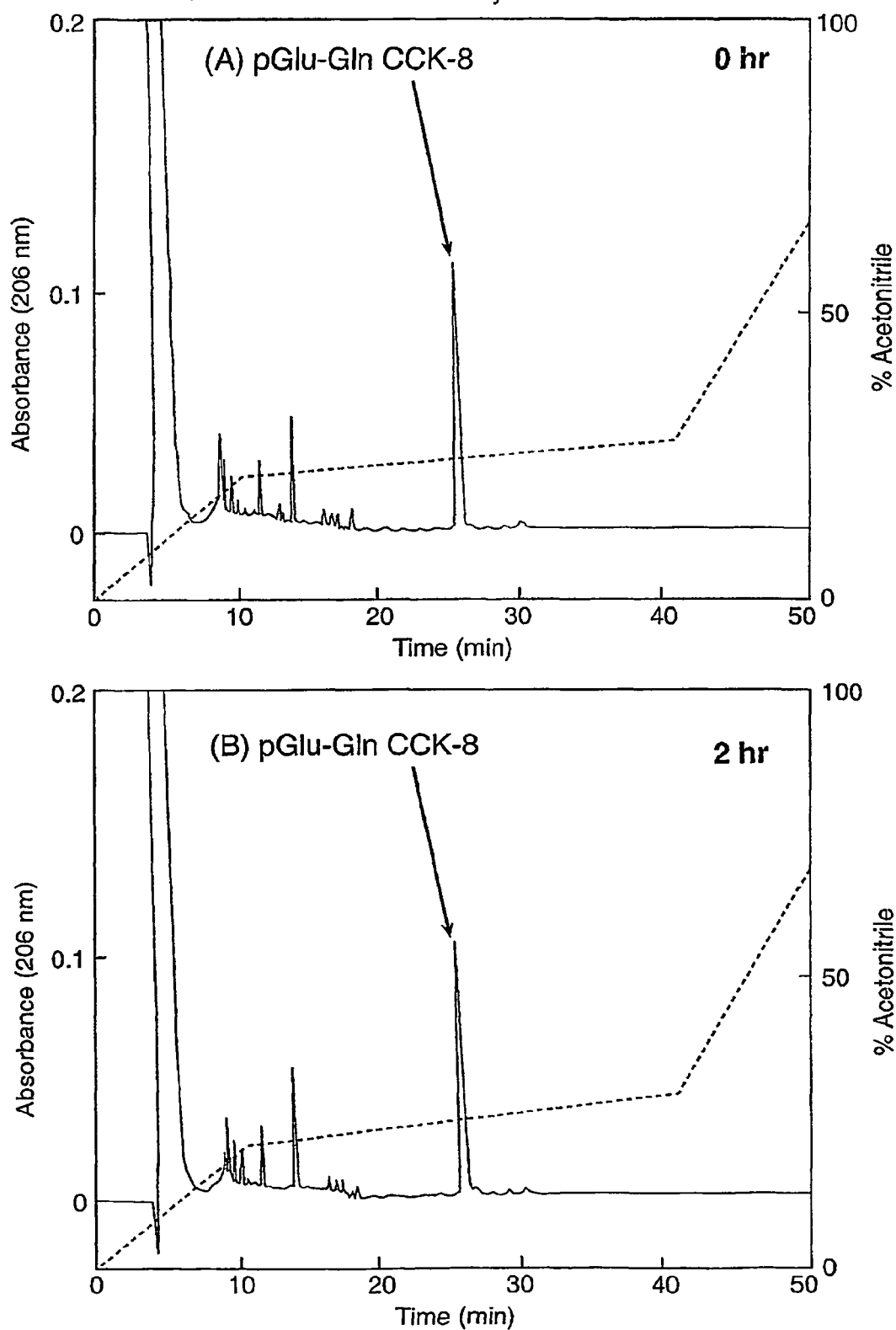
Fig. 2. HPLC profiles of pGlu-Gln CCK-8 following incubation with serum for 0 and 2 h on a Vydac C-18 column

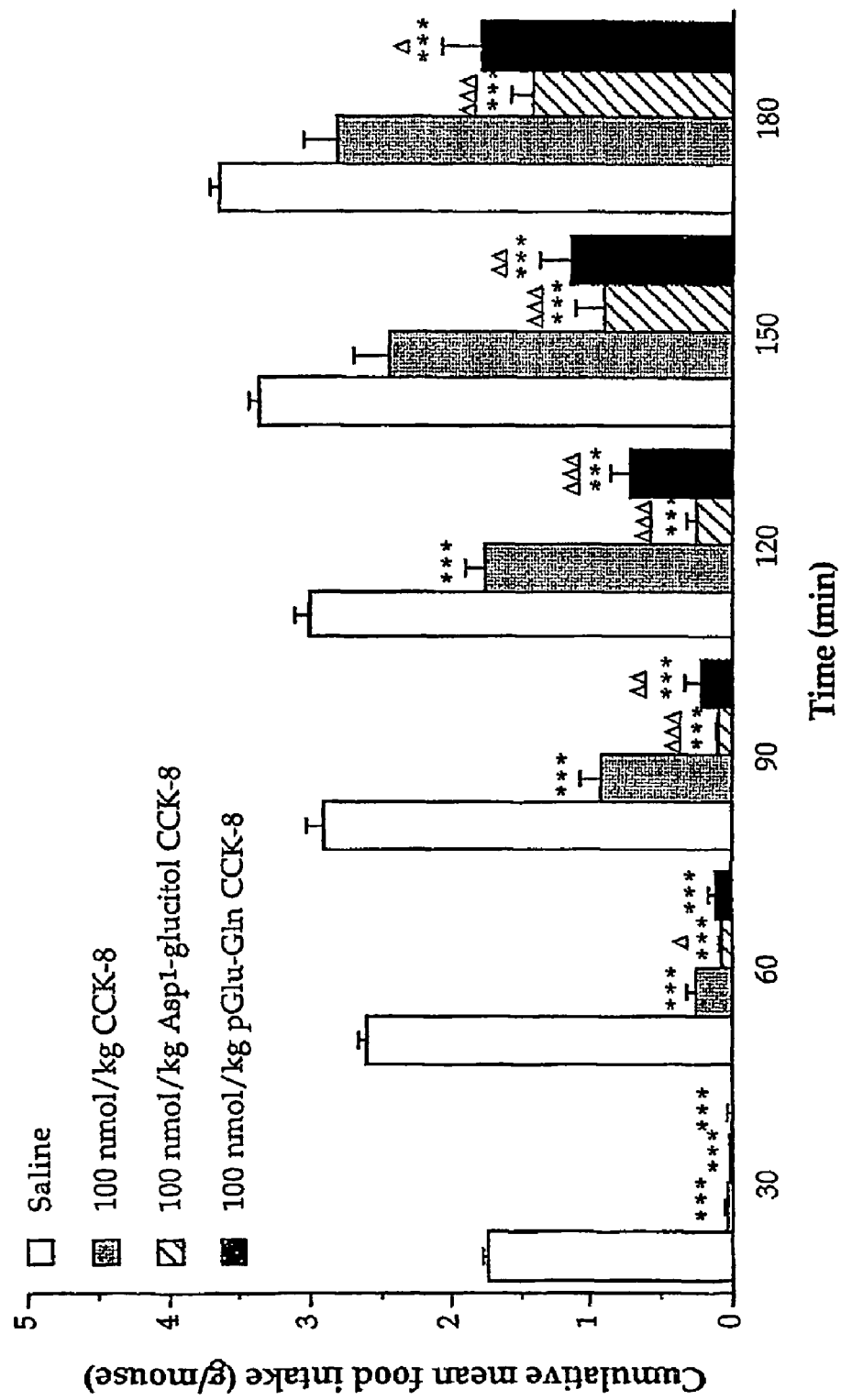

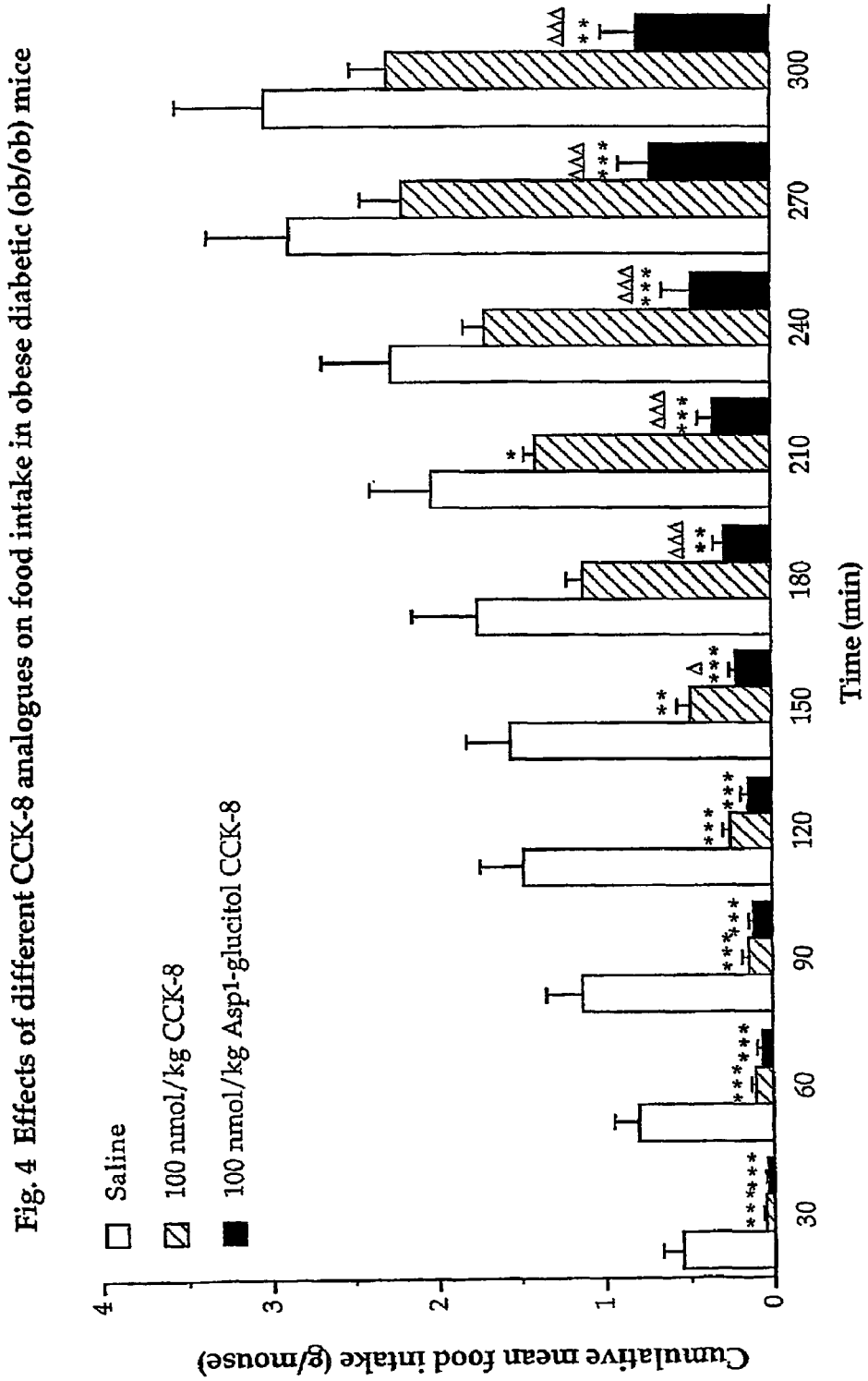

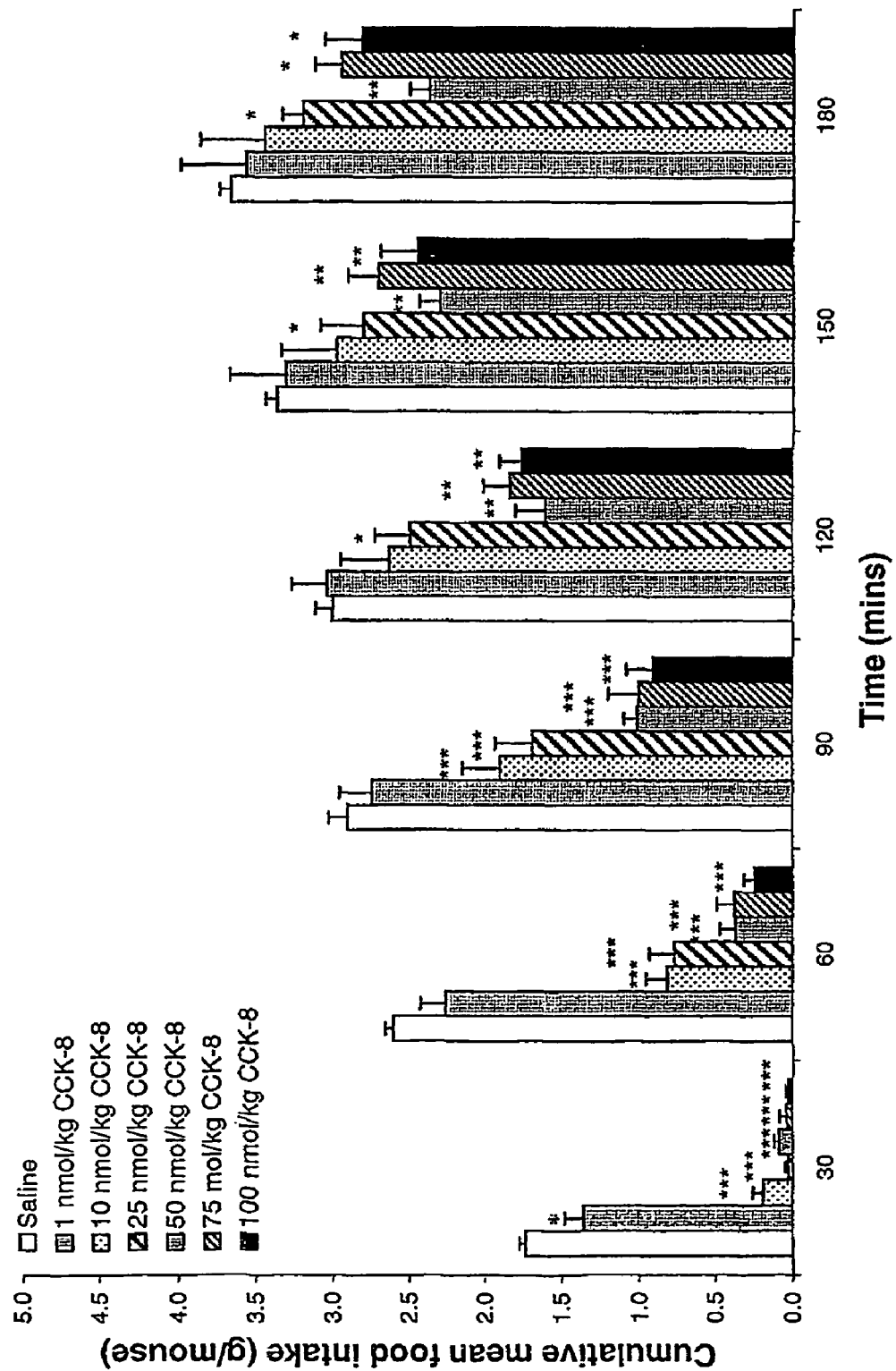

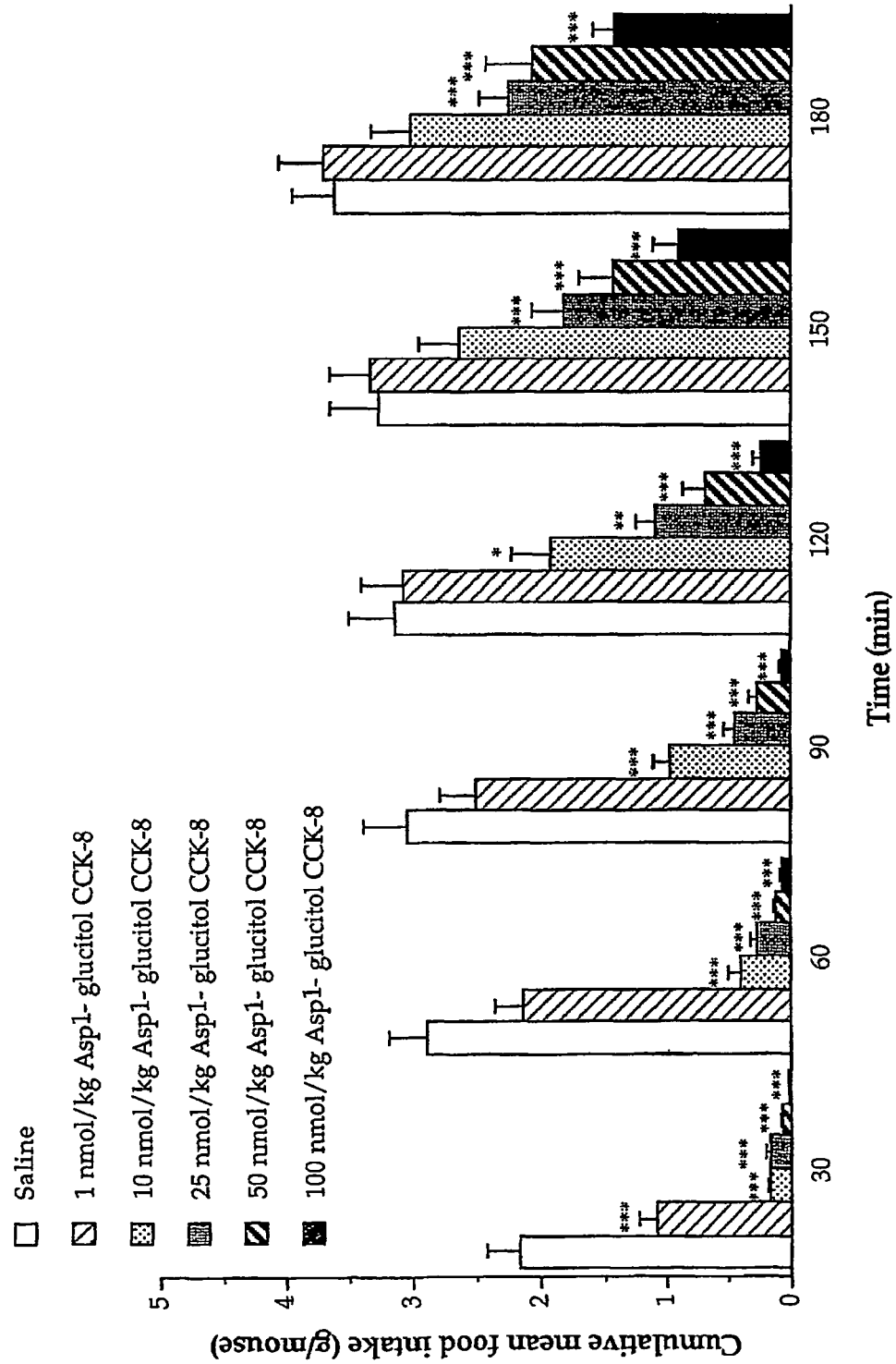
Fig. 6 Effects of different doses of Asp1-glucitol CCK-8 on food intake

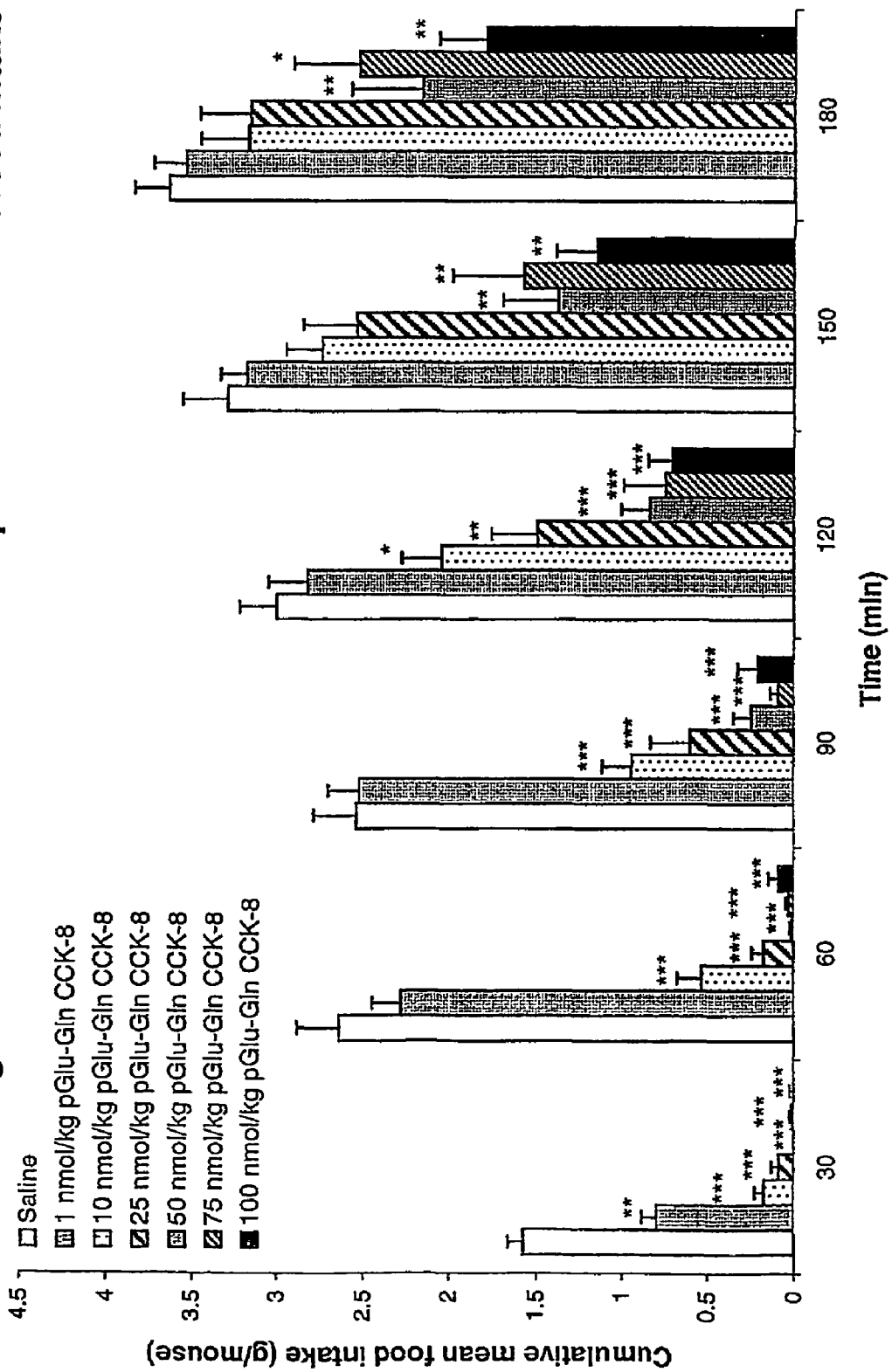

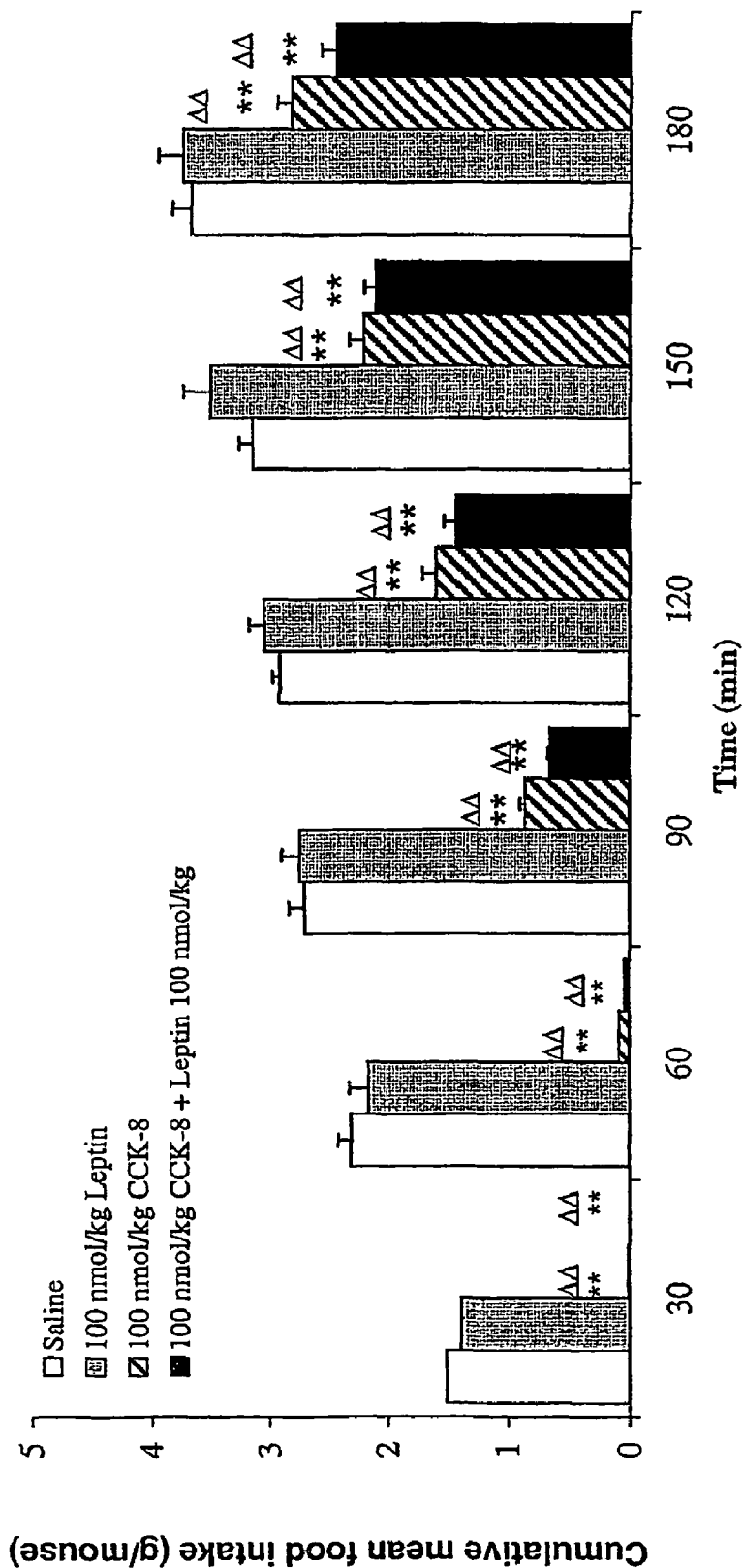

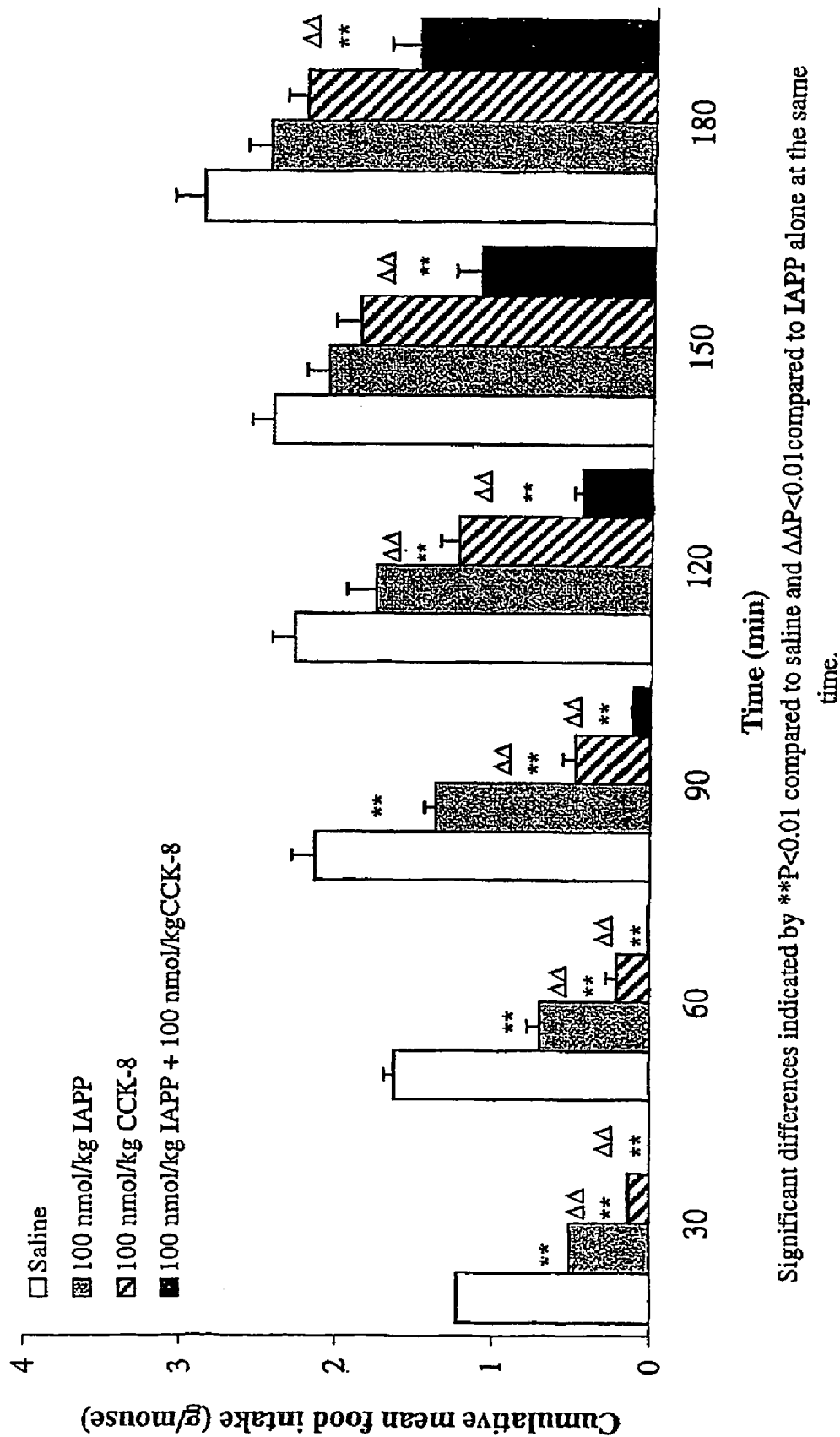

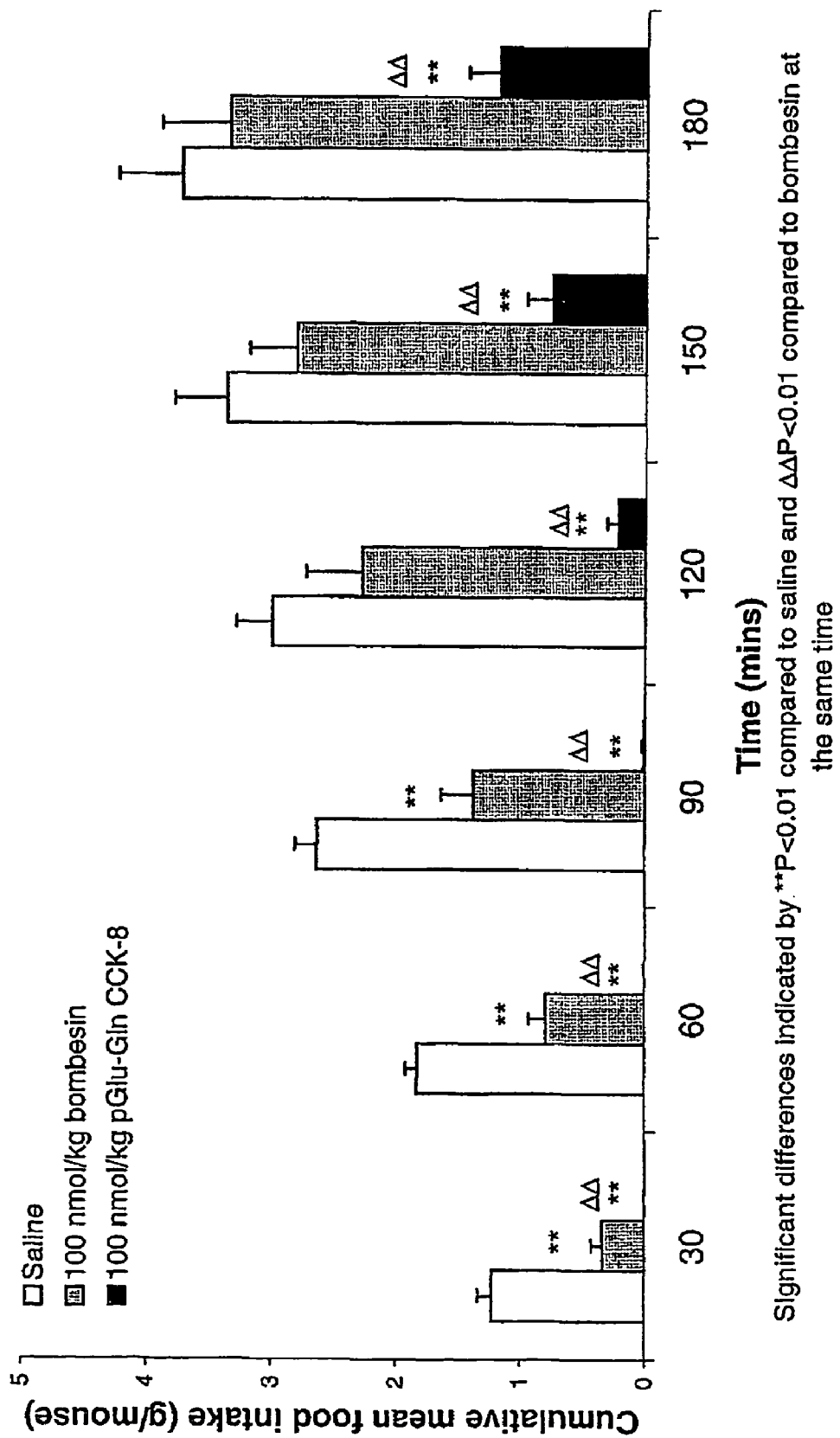

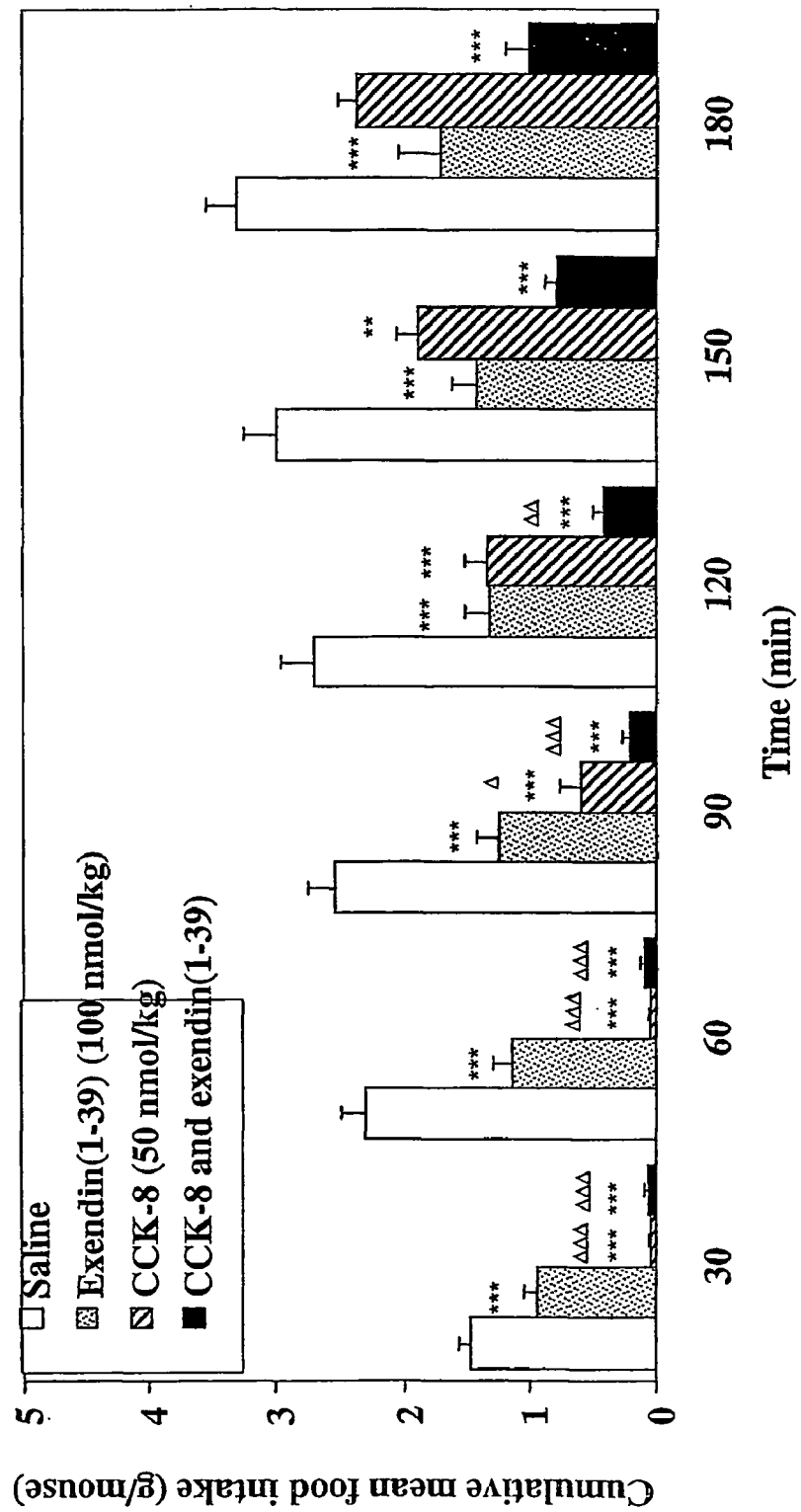

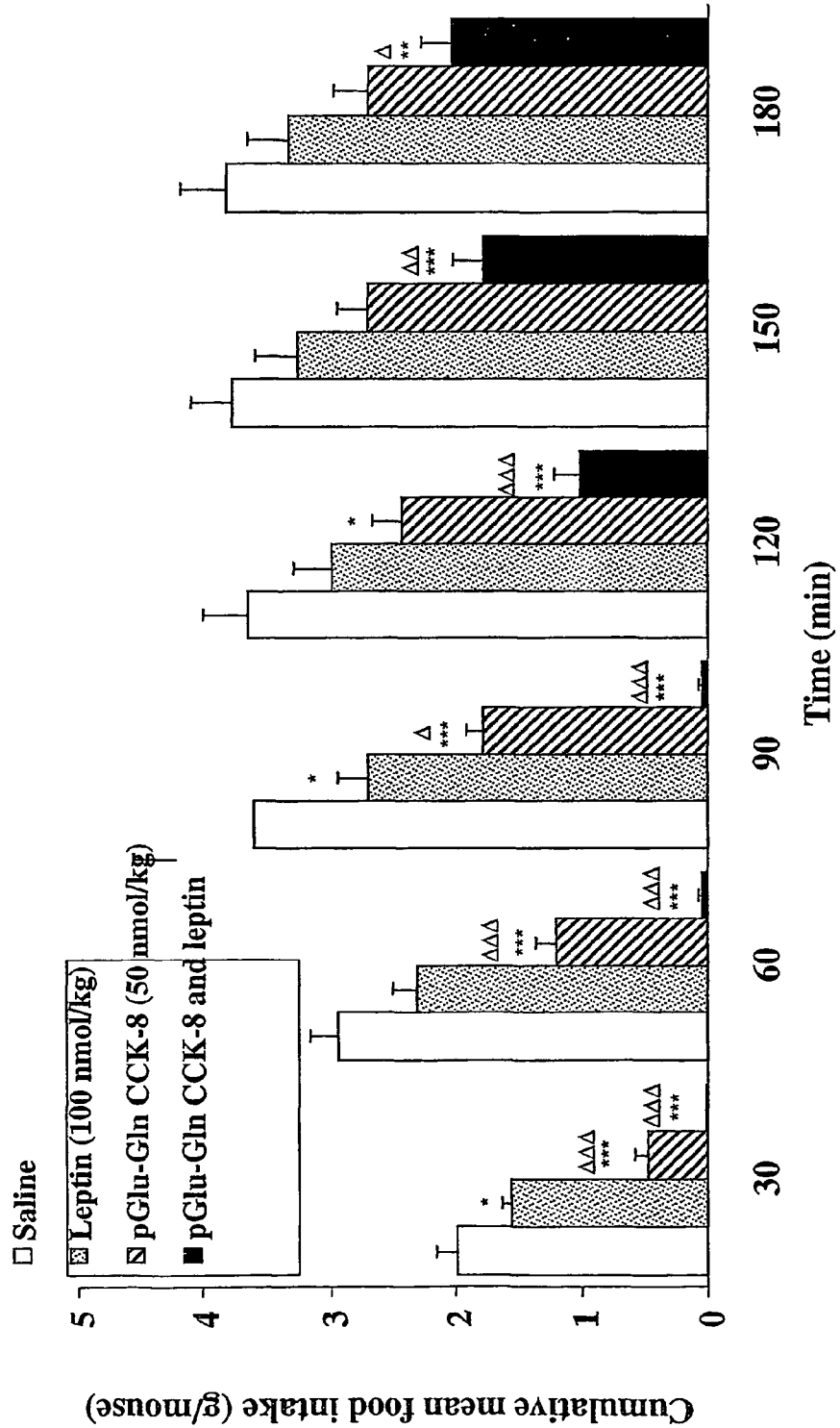
Fig. 12 Effects of leptin (120μg/kg) and pGlu-Gln CCK-8 on food intake

```
                          SEQUENCE LISTING

<160> NUMBER OF SEQ ID NOS: 1

<210> SEQ ID NO 1
<211> LENGTH: 8
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: SULFATATION
<220> FEATURE:
<221> NAME/KEY: MOD_RES
<222> LOCATION: (8)..(8)
<223> OTHER INFORMATION: AMIDATION

<400> SEQUENCE: 1

Asp Tyr Met Gly Trp Met Asp Phe
1               5
```

MODIFIED PEPTIDE

The present invention relates to the regulation of feeding and control of energy metabolism. More particularly the invention relates to the use of peptides to suppress food intake and pharmaceutical preparations for the treatment of obesity and type 2 diabetes.

Cholecystokinin (CCK), is a neuropeptide hormone found in the brain and secreted from gut endocrine cells, which was originally identified from its ability to stimulate gall bladder contraction. CCK is now known to play a significant role in many physiological processes including regulation of satiety, bowel motility, gastric emptying, insulin secretion, pancreatic enzyme secretion and neurotransmission. CCK exists in multiple molecular forms in the circulation ranging from 58, 39, 33, 22, 8 and 4 amino acids in length. CCK-33 was the original form purified from porcine intestine. The C-terminal octapeptide CCK-8 is well conserved between species and is the smallest form that retains the full range of biological activities. A variety of CCK molecular forms are secreted following ingestion of dietary fat and protein, from endocrine mucosal I cells that are mainly located in the duodenum and proximal jejunum. Once released CCK-8 exerts its biological action on various target tissues within the body in a neurocrine, paracrine or endocrine manner. These actions are mediated through two major receptor sub-populations $CCK_A$ (peripheral subtype) and $CCK_B$ (brain subtype). Specific receptor antagonists such as proglumide have aided our understanding of the action of CCK on food intake.

Involvement of CCK in the control of food intake in rodents was recognised in the early 1970's, and since then this peptide hormone has been shown to reduce feeding in man and in several animal species. The induction of satiety is a common feature in different species but the mechanism by which this is achieved is poorly understood. However, many different tissues are known to possess specific receptors for CCK including the vagus nerve, pyloric sphincter and brain all of which may be implicated in this control mechanism. It has been proposed that CCK stimulates receptors in the intestine that activate the vagus nerve, which relays a message to the satiety centres in the hypothalamus. In support of this concept, it has been found that satiety effects of CCK are eliminated in vagotomized animals. Furthermore, rodent studies have indicated that CCK has a more potent satiating ability when administered by the intraperitoneal route rather than centrally. Intraperitoneal CCK-8 is thought to act locally rather than hormonally. In addition, it is known that CCK-8 does not cross the blood brain barrier.

Nevertheless, other evidence suggests that CCK has a definite neuronal influence on food intake in the central nervous system. Some work in dogs has suggested that circulating levels of CCK were too low to induce satiety effects. However, studies in pigs immunized against CCK revealed that these animals increased their food intake and had accelerated weight gain compared to control animals. In addition CCK receptor antagonists increased food intake in pigs and decreased satiety in humans. Overall the above studies indicate that CCK plays a significant role in regulating food intake in mammals.

CCK-8 has been considered as a short-term meal-related satiety signal whereas the recently discovered OB gene product leptin, is more likely to act as an adiposity signal which may reduce total food intake over the longer term. Indeed some workers have suggested that CCK-8 and leptin act synergistically to control long term feeding in mice.

The present invention aims to provide effective analogues of CCK-8. It is one aim of the invention to provide pharmaceuticals for treatment of obesity and/or type 2 diabetes.

According to the present invention there is provided an effective peptide analogue of the biologically active CCK-8 which has improved characteristics for the treatment of obesity and/or type 2 diabetes wherein the analogue has at least one amino acid substitution or modification and not including $Asp^1$-glucitol CCK-8.

The primary structure of human CCK-8 is shown below:

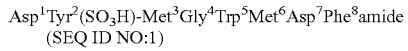

(SEQ ID NO:1)

The analogue may include modification by fatty acid addition (eg. palmitoyl) at the alpha amino group of $Asp^1$ or an epsilon amino group of a substituted lysine residue. The invention includes $Asp^1$-glucitol CCK-8 having fatty acid addition at an epsilon amino group of at least one substituted lysine residue.

Analogues of CCK-8 may have an enhanced capacity to inhibit food intake, stimulate insulin secretion, enhance glucose disposal or may exhibit enhanced stability in plasma compared to native CCK-8. They may also possess enhanced resistance to degradation by naturally occurring exo- and endo-peptidases.

Any of these properties will enhance the potency of the analogue as a therapeutic agent.

Analogues having one or more D-amino acid substitutions within CCK-8 and/or N-glycated, N-alkylated, N-acetylated, N-acylated, N-isopropyl, N-pyroglutamyl amino acids at position 1 are included.

Various amino acid substitutions including for example, replacement of $Met^3$ and/or $Met^6$ by norleucine or 2-aminohexanoic acid. Various other substitutions of one or more amino acids by alternative amino acids including replacing $Met^3$ by Thr, $Met^6$ by Phe, $Phe^8$ by N-methyl Phe.

Other stabilised analogues include those with a peptide isostere bond replacing the normal peptide bond between residues 1 and 2 as well as at any other site within the molecule. Furthermore, more than one isostere bond may be present in the same analogue. These various analogues should be resistant to plasma enzymes responsible for degradation and inactivation of CCK-8 in vivo. including for example aminopeptidase A.

In particular embodiments, the invention provides a peptide which is more potent than CCK-8 in inducing satiety, inhibiting food intake or in moderating blood glucose excursions, said peptide consisting of CCK(1-8) or smaller fragment with one or more modifications selected from the group consisting of:

(i) N-terminal extension of CCK-8 by pGlu-Gln
(ii) N-terminal extension of CCK-8 by pGlu-Gln with substitution of $Met^8$ by Phe.
(iii) N-terminal extension of CCK-8 by Arg
(iv) N-terminal extension of CCK-8 by pyroglutamyl (pGlu)
(v) substitution of the penultimate $Tyr^2(SO_3H)$ by a phosphorylated Tyr
(vi) substitution of the penultimate $Tyr^2(SO_3H)$ by Phe ($pCH_2SO_3Na$)
(vii) substitution of a naturally occurring amino acid by an alternative amino acid including; $Met^3$ and/or $Met^6$ by norleucine or 2-aminohexanoic acid, $Met^3$ by Thr, $Met^6$ by Phe, $Phe^8$ by N-methyl Phe
(viii) substitution described in (vii) above with or without N-terminal modification of $Asp^1$ (eg. by acetylation, glycation, acylation, alkylation, pGlu-Gln etc).
(ix) modification of $Asp^1$ by acetylation
(x) modification of $Asp^1$ by acylation (eg. palmitate)
(xi) modification of a substituted Lys residue by a fatty acid (eg. palmitate)
(xii) modification of $Asp^1$ by alkylation
(xiii) modification of $Asp^1$ by glycation in addition to a fatty acid (eg. palmitate) linked to an epsilon amino group of a substituted Lys residue (xiv) modification of Asp$^1$ by isopropyl
(xv) modification of Asp$^1$ by Fmoc or Boc
(xvi) conversion of Asp$^1$-Tyr$^2$ bond to a stable non-peptide isostere bond CH$_2$NH
(xvii) conversion of Tyr$^2$-Met$^3$ bond to a psi [CH$_2$NH] bond
(xviii) conversion of Met$^3$-Gly$^4$ bond to a psi [CH$_2$NH] bond
(xix) conversion of Met$^6$-Asp$^7$ bond to a psi [CH$_2$NH] bond
(xx) conversion of other peptide bonds to a psi [CH$_2$NH] bond
(xxi) modification of Tyr$^2$ by acetylation (i.e. acetylated CCK-7)
(xxii) modification of Tyr$^2$ by pyroglutamyl (i.e. pyroglutamyl CCK-7)
(xxiii) modification of Tyr$^2$ by glycation (i.e. glycated CCK-7)
(xxiv) modification of Tyr$^2$ by succinic acid (i.e. succinyl CCK-7)
(xxv) modification of Tyr$^2$ by Fmoc (i.e. Fmoc CCK-7)
(xxvi) modification of Tyr$^2$ by Boc (i.e. Boc CCK-7)
(xxvii) D-amino acid substituted CCK-8 at one or more sites
(xxviii) D-amino acid substituted CCK-8 at one or more sites in addition to an N-terminal modification by for example acetylation, acylation, glycation etc
(xxix) reteroinverso CCK-8 (substituted by D-amino acids throughout octapeptide and primary structure synthesised in reverse order)
(xxx) shortened N- and/or C-terminal truncated forms of CCK-8 and cyclic forms of CCK-8
(xxxi) The invention also provides a method of N-terminally modifying CCK-8 or analogues thereof during synthesis. Preferably the agents would be glucose, acetic anhydride or pyroglutamic acid.

The invention also provides the use of Asp$^1$-glucitol CCK-8, pGlu-Gln CCK-8 and other analogues in the preparation of medicament for treatment of obesity and/or type 2 diabetes.

The invention further provides improved pharmaceutical compositions including analogues of CCK-8 with improved pharmacological properties.

Other possible analogues include truncated forms of CCK-8 represented by removal of single or multiple amino acids from either the C- or N-terminus in combination with one or more of the other modifications specified above.

According to the present invention there is also provided a pharmaceutical composition useful in the treatment of obesity and/or type 2 diabetes which comprises an effective amount of the peptide as described herein, in admixture with a pharmaceutically acceptable excipient for delivery through transdermal, nasal inhalation, oral or injected routes. Said peptide to be administered alone or in combination therapy with native or derived analogues of leptin, islet amyloid polypeptide (IAPP) or bombesin (gastrin-releasing peptide).

The invention also provides a method of N-terminally modifying CCK-8 and analogues thereof. This 3 step process firstly involving solid phase synthesis of the C-terminus up to Met$^3$. Secondly, adding Tyr(tBu) to a manual bubbler system as an Fmoc-protected PAM resin, deprotecting the Fmoc by piperidine in DMF and reacting with an Fmoc protected Asp (OtBu)-OH, allowing the reaction to proceed to completion, removal of the Fmoc protecting group from the dipeptide, reacting the dipeptide with the modifying agent (eg. glucose, acetic anhydride, palmitate, etc), removal of side-chain protecting groups (tBu and OtBu) by acid, sulphating the Tyr$^2$ with sulphur trioxide, cleaving the peptide from the resin under alkaline conditions. Thirdly, the N-terminal modified dipeptide can be added to the C-terminal peptide resin in the synthesizer, followed by cleavage from the resin under alkaline conditions with methanolic ammonia, and finally purification of the final product using standard procedures.

The invention will now be demonstrated with reference to the following non-limiting examples and the accompanying figures wherein:

FIG. 1 illustrates the degradation of CCK-8 and Asp$^1$-glucitol CCK-8 by plasma.

FIG. 2 illustrates the lack of degradation of pGlu-Gln CCK-8 by plasma.

FIG. 3 illustrates the effect of CCK-8, Asp$^1$-glucitol CCK-8 and pGlu-Gln CCK-8 on food intake.

FIG. 4 illustrates the effect of CCK-8 and Asp$^1$-glucitol CCK-8 on food intake in ob/ob mice.

FIG. 5 illustrates the effect of different doses of CCK-8 on food intake.

FIG. 6 illustrates the effect of different doses of Asp$^1$-glucitol CCK-8 on food intake.

FIG. 7 illustrates the effect of different doses of pGlu-Gln CCK-8 on food intake.

FIG. 8 illustrates the effect of CCK-8 and leptin both alone and combined on food intake.

FIG. 9 illustrates the effect of CCK-8 and IAPP both alone and combined on food intake.

FIG. 10 illustrates the effect of bombesin and pGlu-Gln CCK-8 on food intake.

FIG. 11 illustrates the effect of pGlu-Gln CCK-8 and leptin both alone and combined on food intake.

FIG. 12 illustrates the effect of pGlu-Glin CCK-8 and leptin both alone and combined on food intake.

EXAMPLE 1

Preparation of N-Terminally Modified CCK-8 and Analogues Thereof

The N-terminal modification of CCK-8 is essentially a three step process. Firstly, CCK-8 is synthesised from its C-terminal (starting from an Fmoc-Phe-OCH$_2$-PAM-Resin, Novabiochem) up to Met$^3$ on an automated peptide synthesizer (Applied Biosystems, CA, USA). The synthesis follows standard Fmoc peptide chemistry protocols utilizing other protected amino acids in a sequential manner used including Fmoc-Asp(OtBu)-OH, Fmoc-Met-OH, Fmoc-Trp-OH, Fmoc-Gly-OH, Fmoc-Met-OH. Deprotection of the N-terminal Fmoc-Met will be performed using piperidine in DMF (20% v/v). The OtBu group will be removed by shaking in TFA/Anisole/DCM. Secondly, the penultimate N-terminal amino acid of native CCK-8 (Tyr(tBu) is added to a manual bubbler system as an alkali labile Fmoc-protected Tyr(tBu)-PAM resin. This amino acid is deprotected at its N-terminus (piperidine in DMF (20% v/v)). This is then allowed to react with excess Fmoc-Asp(OtBu)-OH forming a resin bound dipeptide Fmoc-Asp(OtBu)-Tyr(tBu)-PAM resin. This will be deprotected at its N-terminus (piperidine in DMF (20% v/v)) leaving a free α-amino group. This will be allowed to react with excess glucose (glycation, under reducing conditions with sodium cyanoborohydride), acetic anhydride (acetylation), pyroglutamic acid (pyroglutamyl) etc. for up to 24 hours as necessary to allow the reaction to go to completion. The completeness of reaction will be monitored using the ninhydrin test which will determine the presence of available free α-amino groups. Deprotection of the side-chains will be achieved by shaking in TFA/Anisole/DCM. Sulphation of the N-terminally modified dipeptide will be achieved by suspending the peptide in DMF/pyridine and adding sulphur trioxide-pyridine complex with shaking up to 24 hours. Once the reaction is complete, the now structurally modified N-terminal dipeptide, containing the sulphated Tyr, will be cleaved from the PAM resin (under basic conditions with methanolic ammonia) and with appropriate scavengers. Thirdly, a 4-fold excess of the N-terminally modified-Asp-Tyr(SO$_3$H)—OH will be added directly to the automated peptide synthesizer, which will carry on the synthesis, thereby stitching the N-terminally modified-region to the α-amino of CCK(Met³), completing the synthesis of the sulphated CCK analogue. This peptide is cleaved off the PAM resin (as above under alkaline conditions) and then worked up using the standard Buchner filtering, precipitation, rotary evaporation and drying techniques. The filtrate will be lyophilized prior to purification on a Vydac semi-preparative C-18 HPLC column (1.0×25 cm). Confirmation of the structure of CCK-8 related analogues will be performed by mass spectrometry (ESI-MS and/or MALDI-MS).

EXAMPLE 2

Effects of CCK-8 Analogues on Food Intake

The following example investigates preparation of Asp¹-glucitol CCK-8 and pGlu-Gln CCK-8 together with evaluation of their effectiveness at inducing satiety and decreasing food intake in vivo. The results clearly demonstrate that these novel analogues exhibit substantial resistance to aminopeptidase degradation and increased biological activity compared with native CCK-8.

Research Design and Methods

Materials. Cholecystokinin octapeptide (sulphated CCK-8), pGlu-Gln CCK-8 and other analogues will be synthesised using an Applied Biosystems 432 Peptide synthesizer (as described above). HPLC grade acetonitrile was obtained from Rathburn (Walkersburn, Scotland). Sequencing grade trifluoroacetic acid (TFA) was obtained from Aldrich (Poole, U.K.). All water used in these experiments was purified using a Milli-Q, Water Purification System (Millipore Corporation, Millford, Mass., U.S.A.). All other chemicals purchased were from Sigma, Poole, UK.

Preparation of Asp¹glucitol CCK-8 and pGlu-Gln CCK-8. Asp¹-glucitol CCK-8 and pGlu-Gln CCK-8 were prepared by a 3 step process as described in example 1. The peptides were purified on a Vydac semi-preparative C-18 HPLC column (1.0×25 cm) followed by a C-18 analytical column using gradient elution with acetonitrile/water/TFA solvents. Confirmation of the structure of CCK-8 related analogues was by mass spectrometry (ESI-MS and/or MALDI-MS). Purified control and structurally modified CCK-8 fractions used for animal studies were quantified (using the Supelcosil C-8 column) by comparison of peak areas with a standard curve constructed from known concentrations of CCK-8 (0.78-25 μg/ml).

Molecular mass determination of Asp¹glucitol CCK-8 and pGlu-Gln CCK-8 by electrospray ionization mass spectrometry (ESI-MS). Samples of CCK-8 and structurally modified CCK-8 analogues were purified on reversed-phase HPLC. Peptides were dissolved (approximately 400 pmol) in 100 μl of water and applied to the LCQ benchtop mass spectrometer (Finnigan MAT, Hemel Hempstead, UK) equipped with a microbore C-18 HPLC column (150×2.0 mm, Phenomenex, UK, Ltd., Macclesfield). Samples (30 μl direct loop injection) were injected at a flow rate of 0.2 ml/min, under isocratic conditions 35% (v/v) acetonitrile/water. Mass spectra were obtained from the quadripole ion trap mass analyzer and recorded. Spectra were collected in the positive and negative mode using full ion scan mode over the mass-to-charge (m/z) range 150-2000. The molecular masses of positive ions from CCK-8 and related analogues were determined from ESI-MS profiles using prominent multiple charged ions and the following equation $M_r=iM_i-iM_h$ (where $M_r$=molecular mass; $M_i$=m/z ratio; i=number of charges; $M_h$=mass of a proton).

Effects of CCK-8, Asp¹glucitol CCK-8, pGlu-Gln CCK-8 and other peptides on food intake in mice. Studies to evaluate the relative potencies of control CCK-8, Asp¹-glucitol CCK-8, pGlu-Gln CCK-8 and other peptides involved in regulation of feeding were performed using male Swiss TO mice (n=16) aged 7-12 weeks from a colony originating from the Behavioral and Biomedical Research Unit, University of Ulster. The animals were housed individually in an air-conditioned room at 22±2° C. with 12 h light/12 h dark cycle. Drinking water was supplied ad libitum and standard mouse maintenance diet (Trouw Nutrition, Cheshire, UK) was provided for various times as indicated below. The mice were habituated to a daily feeding period of 3 h/day by progressively reducing the feeding period over a 3 week period. On days 1-6, food was supplied from 10.00 to 20.00 h, days 7-14 from 10.00 to 16.00 h and days 15-21 food was restricted to 10.00 to 13.00 h. Body weight, food and water intake were monitored daily.

Mice which had been previously habituated to feeding for 3 h/day were administered a single i.p. injection of saline (0.9% w/v NaCl, 10 ml/kg) in the fasted state (10.00 h) and food was immediately returned following injection. Two days after the saline injection, mice were randomly allocated into groups of 7-8 animals which were administered a single i.p. injection (from 1 to 100 nmol/kg) of either CCK-8, structurally modified CCK-8 analogues and/or other peptide hormones (including, bombesin, leptin and islet amyloid polypeptide (IAPP)). Food intake was carefully monitored at 30 min intervals up to 180 min post injection. In one series of experiments, the ability of CCK-8 and Asp¹-glucitol CCK-8 to inhibit feeding activity was studied in overnight fasted adult obese hyperglycaemic (ob/ob) mice. All animal studies were done in accordance with the Animals (Scientific Procedures) Act 1986.

Effects of mouse serum on degradation of CCK-8, Asp¹glucitol CCK-8 and pGlu-Gln CCK-8. Serum (20 μl) from fasted Swiss TO mice was incubated at 37° C. with 10 μg of either native CCK-8, Asp¹-glucitol CCK-8 or pGlu-Gln CCK-8 for periods up to 2 h in a reaction mixture (final vol. 500 μl) containing 50 mmol/l triethanolamine/HCl buffer pH 7.8. The reaction was stopped by addition of 5 μl of TFA and the final volume adjusted to 1.0 ml using 0.1% (v/v) TFA/water. Samples were centrifuged (13,000 g, 5 min) and the supernatant applied to a C-18 Sep-Pak cartridge (Waters/Millipore) which was previously primed and washed with 0.1% (v/v) TFA/water. After washing with 20 ml 0.12% TFA/water, bound material was released by elution with 2 ml of 80% (v/v) acetonitrile/water and concentrated using a Speed-Vac concentrator (AES 1000, Savant). The volume was adjusted to 1.0 ml with 0.12% (v/v) TFA/water and applied to a (250×4.6 mm) Vydac C-18 column pre-equilibrated with 0.12% (v/v) TFA/water at a flow rate of 1.0 ml/min. The concentration of acetonitrile in the eluting solvent was raised from 0 to 31.5% over 15 min, from 31.5 to 38.5% over 30 min, and from 38.5 to 70% over 5 min, using linear gradients monitoring eluting peaks at 206 nm.

Statistical analysis. Groups of data are presented as means±SE. Statistical evaluation was performed using analysis of variance, least significant difference multiple comparisons test and Student's unpaired t-test as appropriate. Differences were considered to be significant if P<0.05.

Results

Molecular mass determination. Following incubation, Asp¹-glucitol CCK-8 and pGlu-Gln CCK-8 were clearly separated from native CCK-8 on a Vydac C-18 HPLC column. The average molecular masses of CCK-8 ($M_r$ 1064.2), Asp¹-glucitol CCK-8 ($M_r$ 1228.4) and pGlu-Gln CCK-8 ($M_r$ 1352.4) were determined by ESI-MS, confirming their structures.

In vitro degradation of CCK-8, Asp¹glucitol CCK-8 and pGlu-Gln CCK-8. FIG. 1 shows a comparison of typical examples of HPLC traces following the action of mouse serum in vitro on the degradation of CCK-8 (left panels) or Asp¹ glucitol CCK-8 (right panels) at time 0, 1 and 2 h. Intact CCK-8 (peak A) and three separate fragments of CCK-8 (peaks B, C, D) eluted at 22.18, 22.01, 19.81 and 18.98 min, respectively. Asp¹ glucitol CCK-8 (peak E, right panels) eluted at 21.65 min. Table 1 summarises the pattern of CCK-8 and Asp¹ glucitol CCK-8 breakdown in each case. From analysis of HPLC peak area data it is evident that 83.1% and 100% of the CCK-8 was converted to the CCK-8 fragments after 1 and 2 h incubation, respectively. In contrast, Asp¹-glucitol CCK-8 remained intact after 1 and 2 h incubation and no additional peptide fragments were detected. Similarly, pGlu-Gln CCK-8 was also highly resistant to plasma degradation after 2 h (FIG. 2).

Food intake trials. The daily food intake of mice during the period before administration of peptides indicated that mean food consumption of the mice allowed 3 h access to food was 3.8±0.2 g/mouse. Following administration of i.p. saline, there was no significant difference in 3 h voluntary food intake (3.66±0.1 g) when compared to 3 h food intake alone. FIG. 3 shows that i.p. injection with CCK-8 had an inhibitory effect on voluntary food intake at 30, 60 and 90 min post treatment compared to saline alone. However, there was no sustained inhibitory action of CCK-8 on cumulative food intake beyond 90 min. In contrast, the inhibitory effect of Asp¹-glucitol CCK-8 and pGlu-Gln CCK-8 on food intake was sustained over the 3 h post-treatment feeding period compared to saline response. Furthermore, both structurally modified CCK-8 peptides were significantly more potent at reducing food intake at each time point (except at 30 min) compared to the equivalent dose of CCK-8. FIG. 4 shows that CCK-8 and Asp¹-glucitol CCK-8 also significantly reduce voluntary food intake in genetically obese diabetic (ob/ob) mice. Asp¹-glucitol CCK-8 is considerable more potent than native CCK-8.

Dose-response effects of CCK-8, Asp¹-glucitol CCK-8 and pGlu-Gln CCK-8 on food intake are shown in FIGS. 5-7. Compared with CCK-8 both structurally modified peptides exerted more prolonged effects at lower doses. As shown in FIGS. 8-10, CCK-8 or pGlu-Gln CCK-8 were considerably more potent on equimolar basis than either leptin, islet amyloid polypeptide (IAPP) or bombesin in inhibiting food intake over a 30-180 min period. Combination of CCK-8 with either leptin or IAPP, particularly the latter, resulted in a very marked potentiation of satiety action (FIGS. 8-9). FIG. 10 shows that both pGlu-Gln CCK-8 and bombesin are effective anorectic agents but that the former has longer lasting effects. FIG. 11 shows that combination of CCK-8 with exendin(1-39) has particularly enhanced satiety action. Administration of leptin with pGlu-Gln CCK-8 also resulted in a particularly marked and long-lasting inhibition of food intake.

Discussion

The current study examined the effects of CCK-8, Asp¹-glucitol CCK-8 and pGlu-Gln CCK-8 on food intake in mice. The present study demonstrated that CCK-8 was effective in reducing food intake up to 90 min after administration compared to saline controls. The effects of Asp¹-glucitol CCK-8 and pGlu-Gln CCK-8 on food intake were investigated and revealed that these amino-terminally modified peptides had a remarkably enhanced and prolonged ability to reduce voluntary food intake compared to an equimolar dose of native CCK-8. The alteration in primary structure by N-terminal modification of CCK-8 appears to enhance its biological activity and extend its duration of action in normal animals from 90 min to more than 3 h. Indeed the results also indicate that a potent satiety effect can persist for more than 5 h in obese diabetic (ob/ob) mice. The change in biological activity encountered with Asp¹-glucitol CCK-8 and pGlu-Gln CCK-8 extends previous observations that glycation of peptides can alter their biological activities. It is noteworthy that control experiments conducted with glycated tGLP-1 indicate that the presence of a glucitol adduct on the amino-terminus of a peptide, is insufficient on its own to induce satiety in this test system.

The fact that Asp¹-glucitol CCK-8 and pGlu-Gln CCK-8 enhance appetite suppression raises the question of a possible mechanism. Since the very short 1-2 min half-life of CCK-8 is generally accepted as the explanation of the transient satiety effect of the peptide, it is possible that modification of the amino terminus of CCK-8 prolongs the half-life by protecting it against aminopeptidase attack thus enhancing it's activity. Aminopeptidase A has been shown to directly degrade CCK-8 in vivo by hydrolysing the Asp-Tyr bond. The peptide can also be degraded by neutral endopeptidase 24.11 (NEP), thiol or serine endopeptidases and angiotensin converting enzyme. The present study revealed that Asp¹-glucitol CCK-8 and pGlu-Gln CCK-8 were extremely resistant to degradation by peptidases in serum. Thus it seems likely that protection of the amino terminus of CCK-8 with a glucitol or pyroglutamyl-Gln adduct enhances the half-life of glycated CCK-8 in the circulation and thus contributes to enhancement of its biological activity by extending its duration of action in vivo.

Various mechanisms have been proposed to explain the action of CCK in reducing food intake. One hypothesis is that after ingestion of food, gastric distension and nutrient absorption causes release of CCK-8 which ends feeding. It is proposed that CCK-8 both contracts the pyloric sphincter as well as relaxing the proximal stomach which together delays gastric emptying. The gastric branch of the vagus nerve is closely involved in mediating the action of CCK-8. The satiety signal appears to be transmitted from the vagus nerve to the hypothalamus via the nucleus tractus solitarius and the area postrema Although much attention has been given to actions and possible therapeutic use of leptin in obesity and NIDDM, Asp¹-glucitol CCK-8, pGlu-Gln CCK-8 or other structurally modified analogues of CCK-8 may potentially have a number of significant attributes compared with leptin. Firstly, there is accumulating evidence for defects in the leptin receptor and post-receptor signalling in certain forms of obesity-diabetes. Secondly, CCK-8 has potent peripheral actions, whereas leptin acts centrally and requires passage through the blood-brain barrier. Thirdly, the effects of CCK-8 on food intake are immediate whereas the action of leptin requires high dosage and is protracted. Fourthly, CCK has been shown to act as a satiety hormone in humans at physiological concentrations and a specific inhibitor of CCK degradation demonstrates pro-satiating effects in rats. It is also interesting to note that the effects of CCK-8 administered together with either leptin, IAPP, exendin(1-39) or bombesin on satiety are additive, raising the possibility of complementary mechanisms and combined therapies.

In summary, this study demonstrates that CCK-8 can be readily structurally modified at the amino terminus and that intraperitoneally administered Asp¹-glucitol CCK-8 or pGlu-Gln CCK-8, in particular, display markedly enhanced satiating action in vivo, due in part to protection from serum aminopeptidases. These data clearly indicate the potential of N-terminally modified CCK-8 analogues for inhibition of feeding and suggest a possible therapeutic use in humans in the management of obesity and related metabolic disorders.

Figure Legends

FIG. 1 HPLC profiles of CCK-8 and Asp¹-glucitol CCK-8 following incubation with serum for 0, 1 and 2 h on a Vydac C-18 column. Representative traces are shown for CCK-8 (left panels) and Asp¹-glucitol CCK-8 (right panels). Asp¹-glucitol CCK-8 and CCK-8 incubations were separated using linear gradients 0% to 31.5% acetonitrile over 15 min followed by 31.5% to 38.5% over 30 min and 38.5% to 70% acetonitrile over 5 min. Peak A corresponds to intact CCK-8; peaks B, C and D to a CCK-8 fragments; and peak E to Asp$^1$-glucitol CCK-8.

FIG. 2 HPLC profiles of pGlu-Gln CCK-8 following incubation with serum for 0 and 2 h on a Vydac C-18 column. Representative traces are shown for pGlu-Gln CCK-8 after 0 h (left panel) and 2 h (right panel). pGlu-Gln CCK-8 incubations were separated using linear gradients 0% to 31.5% acetonitrile over 15 min followed by 31.5% to 38.5% over 30 min and 38.5% to 70% acetonitrile over 5 min. The eluting single peak at 0 and 2 h corresponds to intact pGlu-Gln CCK-8.

FIG. 3 Effect of CCK-8, Asp$^1$-glucitol CCK-8, pGlu-Gln CCK-8 or saline on voluntary food intake in Swiss TO mice. Saline or test agents were administered by i.p. injection (100 nmol/kg) to fasted mice at time 0 immediately before introduction of food. Cumulative food intake was monitored at 30, 60, 90, 120, 150 and 180 min post injection. Values are means±SE of 7-8 observations (n=16 for saline controls). Significant differences are indicated by *P<0.05, P<0.01, *P<0.001 compared with saline at the same time and ΔP<0.05, ΔΔP<0.01 compared with native CCK-8.

FIG. 4 Effect of CCK-8, Asp$^1$-glucitol CCK-8 or saline on voluntary food intake in obese diabetic (ob/ob) mice. Saline or test agents were administered by i.p. injection (100 nmol/kg) to fasted obese diabetic (ob/ob) mice at time 0 immediately before introduction of food. Cumulative food intake was monitored at 30, 60, 90, 120, 150, 180, 210, 240, 270 and 300 min post injection. Values are means±SE of 8 observations. Significant differences are indicated by *P<0.05, P<0.01, *P<0.001 compared with saline at the same time and ΔP<0.05, ΔΔΔP<0.01 compared with native CCK-8.

FIG. 5 Effect of different doses of CCK-8 or saline on voluntary food intake in Swiss TO mice. Saline or test agents were administered by i.p. injection (1 to 100 nmol/kg) to fasted mice at time 0 immediately before introduction of food. Cumulative food intake was monitored at 30, 60, 90, 120, 150 and 180 min post injection. Values are means±SE of 7-8 observations (n=16 for saline controls): Significant differences are indicated by *P<0.05, P<0.01, *P<0.001 compared with saline at the same time.

FIG. 6 Effect of different doses of Asp$^1$-glucitol CCK-8 or saline on voluntary food intake in Swiss TO mice. Saline or test agents were administered by i.p. injection (1 to 100 nmol/kg) to fasted mice at time 0 immediately before introduction of food. Cumulative food intake was monitored at 30, 60, 90, 120, 150 and 180 min post injection. Values are means±SE of 7-8 observations (n=16 for saline controls). Significant differences are indicated by *P<0.05, P<0.01, *P<0.001 compared with saline at the same time.

FIG. 7 Effect of different doses of pGlu-Gln CCK-8 or saline on voluntary food intake in Swiss TO mice. Saline or test agents were administered by i.p. injection (1 to 100 nmol/kg) to fasted mice at time 0 immediately before introduction of food. Cumulative food intake was monitored at 30, 60, 90, 120, 150 and 180 min post injection. Values are means±SE of 7-8 observations (n=16 for saline controls). Significant differences are indicated by *P<0.05, P<0.01, *P<0.001 compared with saline at the same time.

FIG. 8 Effect of CCK-8, leptin, combined CCK-8 and leptin, as well as saline on voluntary food intake in Swiss TO mice. Saline or test agents were administered alone (100 nmol/kg) or combined (100 nmol/kg of each) by i.p. injection to fasted mice at time 0 immediately before introduction of food. Cumulative food intake was monitored at 30, 60, 90, 120, 150 and 180 min post injection. Values are means±SE of 7-8 observations. Significant differences are indicated by **P<0.01 compared with saline and ••P<0.01 compared to leptin alone at the same time.

FIG. 9 Effect of CCK-8, IAPP, combined CCK-8 and IAPP, as well as saline on voluntary food intake in Swiss TO mice. Saline or test agents were administered alone (100 nmol/kg) or combined (100 nmol/kg of each) by i.p. injection to fasted mice at time 0 immediately before introduction of food. Cumulative food intake was monitored at 30, 60, 90, 120, 150 and 180 min post injection. Values are means±SE of 7-8 observations. Significant differences are indicated by **P<0.01 compared with saline and ΔΔP<0.01 compared to IAPP alone at the same time.

FIG. 10 Effect of pGlu-Gln CCK-8, bombesin, as well as saline on voluntary food intake in Swiss TO mice. Saline or test agents were administered alone (100 nmol/kg) or combined (100 nmol/kg of each) by i.p. injection to fasted mice at time 0 immediately before introduction of food. Cumulative food intake was monitored at 30, 60, 90, 120, 150 and 180 min post injection. Values are means±SE of 7-8 observations. Significant differences are indicated by **P<0.01 compared with saline and ΔΔP<0.01 compared to IAPP alone at the same time.

FIG. 11 Effect of CCK-8, exendin(1-39), combined CCK-8 and exendin(1-39), as well as saline on voluntary food intake in Swiss TO mice. Saline or test agents were administered alone (50 and 100 mmol/kg, respectively) or combined by i.p. injection to fasted mice at time 0 immediately before introduction of food. Comulative food intake was monitored at 30, 60, 90, 120, 150 and 180 min post injection. Values are means±SE of 7-9 observations. Significant differences are indicated by *P<0.05 P<0.01 *P<0.001 compared with saline and ΔP<0.05 ΔΔP<0.01 ΔΔΔP<0.001 compared to exendin(1-39) alone at the same time.

FIG. 12 Effect of pGlu-Gln CCK-8, leptin, combined pGlu-Gln CCK-8 and leptin, as well as saline on voluntary food intake in Swiss TO mice. Saline or test agents wee administered alone (pGlu-Gln CCK-8 50 mmol/kg; leptin 100 nmol/kg) or combined by i.p. injection to fasted mice at time 0 immediately before introduction of food. Cumulative food intake was monitored at 30, 60, 90, 120, 150 and 180 min post injection. Values are means±SE of 7-8 observations. Significant differences are indicated by *P<0.05 P<0.01 *P<0.001 compared with saline and ΔP<0.05 ΔΔP<0.01 ΔΔΔP<0.001 compared to leptin alone at the same time.

TABLE 1

Effect of serum on in vitro degradation of CCK-8 and glycated CCK-8.

| Incubation time (h) | Peak identity | Peak retention time (min) | % Total CCK-like material |
|---|---|---|---|
| | CCK-8 | | |
| 0 | CCK-8 (A) | 22.18 | 100 |
| 1 | CCK-8 fragment (C) | 19.81 | 43.8 |
| | CCK-8 fragment (B) | 22.01 | 39.3 |
| | CCK-8 (A) | 22.18 | 16.9 |
| 2 | CCK-8 fragment (D) | 18.98 | 11.8 |
| | CCK-8 fragment (C) | 19.81 | 29.5 |
| | CCK-8 fragment (B) | 22.01 | 58.7 |
| | CCK-8 (A) | 22.18 | 0 |
| | Glycated CCK-8 | | |
| 0 | Glycated CCK-8 | 21.65 | 100 |
| 1 | Glycated CCK-8 | 21.65 | 100 |
| 2 | Glycated CCK-8 | 21.65 | 100 |

The invention claimed is:

1. An isolated peptide based on biologically active cholecystokinin-8 (CCK-8) (SEQ ID NO: 1), wherein said peptide is SEQ ID NO: 1, wherein pGlu-Gln is attached to the N-terminal Asp.

2. A pharmaceutical composition comprising the peptide of claim 1 in admixture with a pharmaceutically acceptable excipient.

3. The pharmaceutical composition of claim 2, wherein the pharmaceutically acceptable excipient is suitable for delivery through transdermal, nasal inhalation, oral or injected routes.

4. The pharmaceutical composition of claim 2, further comprising native or derived analogues of leptin, exendin, islet amyloid polypeptide or bombesin.

* * * * *